(12) United States Patent
Haddach et al.

(10) Patent No.: US 6,747,034 B2
(45) Date of Patent: Jun. 8, 2004

(54) CRF RECEPTOR ANTAGONISTS AND METHODS RELATING THERETO

(75) Inventors: Mustapha Haddach, San Diego, CA (US); Marion C. Lanier, San Diego, CA (US); Charles Q. Huang, San Diego, CA (US); James R. McCarthy, Zionsville, IN (US)

(73) Assignee: Neurocrine Biosciences, Inc., San Diego, CA (US)

( * ) Notice: Subject to any disclaimer, the term of this patent is extended or adjusted under 35 U.S.C. 154(b) by 141 days.

(21) Appl. No.: 10/016,694

(22) Filed: Nov. 2, 2001

(65) Prior Publication Data

US 2002/0151557 A1 Oct. 17, 2002

Related U.S. Application Data

(60) Provisional application No. 60/245,821, filed on Nov. 3, 2000.

(51) Int. Cl.$^7$ .................. A61K 31/505; A61P 25/00; C07D 239/00
(52) U.S. Cl. ..................... 514/267; 544/251
(58) Field of Search ................. 514/267, 257; 544/251

(56) References Cited

FOREIGN PATENT DOCUMENTS

| | | |
|---|---|---|
| WO | WO 00/27846 | 5/2000 |
| WO | WO 00/27850 | 5/2000 |

*Primary Examiner*—Brenda Coleman
(74) *Attorney, Agent, or Firm*—Seed IP Law Group PLLC

(57) ABSTRACT

CRF receptor antagonists are disclosed which have utility in the treatment of a variety of disorders, including the treatment of disorders manifesting hypersecretion of CRF in a warm-blooded animals, such as stroke.

31 Claims, No Drawings

CRF RECEPTOR ANTAGONISTS AND METHODS RELATING THERETO

CROSS REFERENCE TO RELATED APPLICATION

This application claims the benefit of U.S. Provisional Application No. 60/245,821 filed Nov. 3, 2000.

BACKGROUND OF THE INVENTION

1. Field of the Invention

This invention relates generally to CRF receptor antagonists, and to methods of treating disorders by administration of such antagonists to a warm-blooded animal in need thereof.

2. Description of the Related Art

The first corticotropin-releasing factor (CRF) was isolated from ovine hypothalmi and identified as a 41-amino acid peptide (Vale et al., *Science* 213:1394–1397, 1981). Subsequently, sequences of human and rat CRF were isolated and determined to be identical, but different from ovine CRF in 7 of the 41 amino acid residues (Rivier et al., *Proc. Natl. Acad. Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), α-endorphin, and other pro-opiomelanocortin ("POMC")-derived peptides from the anterior pituitary (Vale et al., *Science* 213:1394–1397, 1981). Briefly, CRF is believed to initiate its biological effects by binding to a plasma membrane receptor which has been found to be distributed throughout the brain (DeSouza et al., *Science* 224:1449–1451, 1984), pituitary (DeSouza et al., *Methods Enzymol.* 124:560, 1986; Wynn et al., *Biochem. Biophys. Res. Comm.* 110:602–608, 1983), adrenals (Udelsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118:1171–1179, 1986) which mediates CRF-stimulated increase in intracellular production of cAMP (Bilezikjian, L. M., and W. W. Vale, *Endocrinology* 113:657–662, 1983). The receptor for CRF has now been cloned from rat (Perrin et al., *Endo* 133(6):3058–3061, 1993), and human brain (Chen et al., *PNAS* 90(19):8967–8971, 1993; Vita et al., *FEBS* 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J. Physiol.* 255:R744, 1988). Furthermore, clinical data suggests that CRF may be hypersecreted in the brain in depression, anxiety-related disorders, and anorexia nervosa. (DeSouza, *Ann. Reports in Med. Chem.* 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyyrazoline derivatives (Abreu et al., U.S. Pat. No. 5,063,245) and substituted 2-aminothiazole derivatives (Courtemanche et al., Australian Patent No. AU-A-41399/93) have been reported as CRF receptor antagonists. These particular derivatives were found to be effective in inhibiting the binding of CRF to its receptor in the 1–10 μM range and 0.1–10 μM range, respectively.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structure (I):

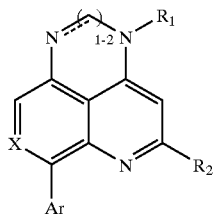

including stereoisomers and pharmaceutically acceptable salts thereof, wherein X, $R_1$, $R_2$ and Ar are as defined below.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists.

In a first embodiment, the CRF receptor antagonists of this invention have the following structure (I):

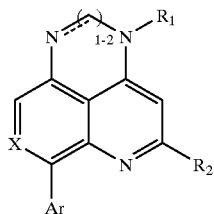

including stereoisomers and pharmaceutically acceptable salts thereof,
wherein:

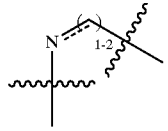

represents —N=CH—, —NH—CH$_2$— or —NH—(CH$_2$)$_2$—;

X is N or CR$_3$;

$R_1$ is —CH($R_4$)($R_5$);

$R_2$ is $C_{1-6}$alkyl;

$R_3$ is hydrogen or $C_{1-6}$alkyl;

$R_4$ is hydrogen, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, or $C_{1-6}$alkyloxy$C_{1-6}$alkly, and $R_5$ is $C_{1-8}$alkyl, mono- or di($C_{3-6}$cycloalkyl)methyl, Ar$^1$CH$_2$, $C_{3-6}$alkenyl, $C_{1-6}$alkyloxy$C_{1-6}$alkyl, hydroxy$C_{1-6}$alkyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl, or a radical of the formula —($C_{1-6}$alkanediyl)—O—CO—Ar$^1$, or $R_4$ and $R_5$ taken together with the carbon atom to which they are bonded form a $C_{5-8}$cycloalkyl optionally substituted with one or more substituents independently selected from $C_{1-6}$alkyl;

Ar is phenyl substituted with 1, 2 or 3 substituents independently selected from halo, $C_{1-6}$alkyl, trifluoromethyl, cyano, $C_{1-6}$alkyloxy, benzyloxy, $C_{1-6}$alkylthio, nitro, amino, and mono- or di($C_{1-6}$alkyl)amino; or an aromatic $C_{3-12}$heterocycle optionally substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino, mono- or di($C_{1-6}$alkyl)amino, and piperidinyl; and Ar$^1$ is phenyl, pyridinyl, or phenyl substituted with 1, 2 or 3 substituents independently selected from halo, $C_{1-6}$alkyl, $C_{1-6}$alkyloxy, di($C_{1-6}$alkyl)amino$C_{1-6}$alkyl, trifluoromethyl and $C_{1-6}$alkyl substituted with morpholinyl.

In the context of this invention, the preceding terms have the meanings set forth below.

"$C_{1-6}$alkyl" or "$C_{1-8}$alkyl" represents a straight chain or branched alkyl having from 1 to 6 carbon atoms or 1 to 8 carbon atoms, respectively, such as methyl, ethyl, n-propyl, isopropyl, n-butyl, tert-butyl, n-pentyl, and the like.

"$C_{1-6}$alkyloxy" represents the group —O($C_{1-6}$alkyl).

"$C_{1-6}$alkylthio" represents the group —S($C_{1-6}$alkyl).

"$C_{3-6}$cycloalkyl" represents a cyclic alkyl having from 3 to 6 carbon atoms, including cyclopropyl, cyclopentyl, cyclopentyl, and cyclohexyl.

"$C_{5-8}$cycloalkyl" represents a cyclic alkyl having from 5 to 8 carbon atoms, such as cyclopentyl, cyclohexyl, and the like.

"$C_{3-6}$alkenyl" represents an unsaturated straight chain or branched alkyl having from 3 to 6 carbon atoms, and having at least one double bond, such as propylene, 1-butene, 2-butene, 2-methylpropene, and the like.

"Hydroxy$C_{1-6}$alkyl" represents a $C_{1-6}$alkyl substituted with at least one hydroxyl group.

"Mono- or di($C_{3-6}$cycloalkyl)methyl" represents a methyl group substituted with one or two $C_{3-6}$cycloalkyl groups, such as cyclopropylmethyl, dicyclopropylmethyl, and the like.

"$C_{1-6}$alkylcarbonyl$C_{1-6}$alkyl" represents a $C_{1-6}$alkyl substituted with a —CO$C_{1-6}$alkyl group.

"$C_{1-6}$alkylcarbonyloxy$C_{1-6}$alkyl" represents a $C_{1-6}$alkyl substituted with a —COO$C_{1-6}$alkyl group.

"$C_{1-6}$alkyloxy$C_{1-6}$alkyl" represents a $C_{1-6}$alkyl substituted with a —O$C_{1-6}$alkyl group.

"$C_{1-6}$alkylthio$C_{1-6}$alkyl" represents a $C_{1-6}$alkyl substituted with a —S$C_{1-6}$alkyl group.

"Mono- or di($C_{1-6}$alkyl)amino represents an amino substituted with one $C_{1-6}$alkyl or with two $C_{1-6}$alkyls, respectively.

"Mono- or di($C_{1-6}$alkyl)amino$C_{1-6}$alkyl" represents a $C_{1-6}$alkyl substituted with a mono- or di($C_{1-6}$alkyl) amino.

"$C_{1-6}$alkanediyl" represents a divalent $C_{1-6}$alkyl radical, such as methylene (—$CH_2$—), ethylene (—$CH_2CH_2$—), and the like.

"$C_{3-12}$heterocycle" represents a ring made up of more than one kind of atom, and which contains 3 to 12 carbon atoms, such as pyridinyl, pyrimidinyl, furanyl, thienyl, imidazolyl, thiazolyl, pyrazolyl, pyridazinyl, pyrazinyl, triazinyl (such as 1,3,5), and the like.

"Halo" means fluoro, chloro, bromo or iodo.

Representative CRF receptor antagonists of this invention include compounds having the following structures (Ia), (Ib) and (Ic):

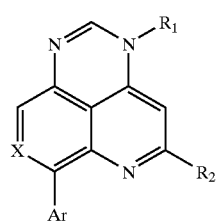
(Ia)

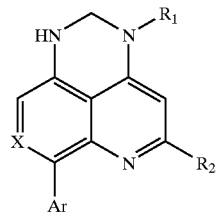
(Ib)

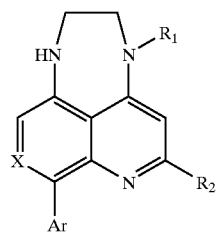
(Ic)

When X of compounds (Ia), (Ib) and (Ic) is N, representative compounds of this invention include the following compounds (Ia'), (Ib') and (Ic'), and when X is $CR_3$, and $R_3$ is hydrogen, representative compounds of this invention include the following compounds (Ia"), (Ib") and (Ic"):

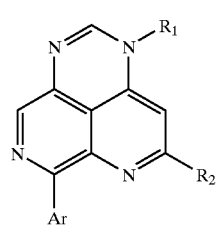
(Ia')

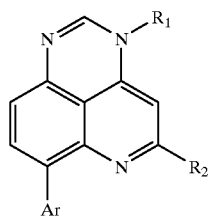
(Ia")

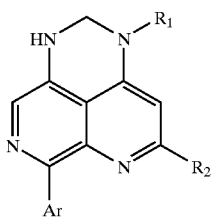
(Ib')

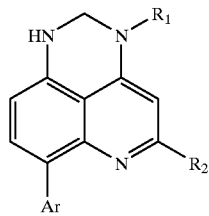
(Ib")

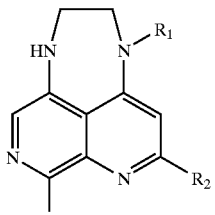
(Ic')

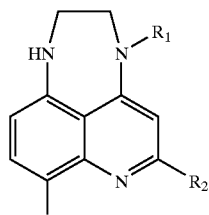
(Ic")

In the embodiment where the $R_4$ and $R_5$ groups of $R_1$ taken together form a $C_{5-8}$cycloalkyl, the resulting $R_1$ group has the structure:

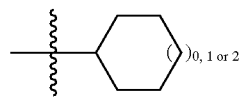

When the above structure is optionally substituted with one or more $C_{1-6}$alkyl groups, a representative $R_1$ moiety has the following structure:

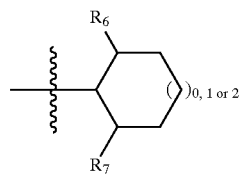

wherein $R_6$ and $R_7$ are the same or different and independently selected from a $C_{1-6}$alkyl, such as methyl or ethyl.

Representative Ar, $R_1$ and $R_2$ groups of this invention are set forth in the following Table. To this end, it should be understood that each combination of the Ar, $R_1$ and $R_2$ groups listed in the following Table 1 represents individual compounds of structure (I), as well as the more specific structures (Ia), (Ib) and (Ic) and sub-structures (Ia'), (Ia''), (Ib'), (Ib''), (Ic') and (Ic'').

TABLE 1

REPRESENTATIVE AR, $R_1$ AND $R_2$ GROUPS OF STRUCTURE (I)

| Ar | $R_1$ | $R_2$ |
|---|---|---|
| 2,4-dichlorophenyl | —CH(n-propyl)$_2$ | —CH$_3$ |
| 2-chloro-4-methyl-phenyl | —CH(n-propyl)$_2$ | —CH$_3$ |
| 2-methyl-4-chloro-phenyl | —CH(n-propyl)$_2$ | —CH$_3$ |
| 2,4,6-trimethyl-phenyl | —CH(n-propyl)$_2$ | —CH$_3$ |
| 2-chloro-4-methoxy-phenyl | —CH(n-propyl)$_2$ | —CH$_3$ |
| 2-methyl-4-methoxy-phenyl | —CH(n-propyl)$_2$ | —CH$_3$ |
| 2,4-dimethoxy-phenyl | —CH(n-propyl)$_2$ | —CH$_3$ |
| 4-dimethylamino-2-methyl-3-pyridyl | —CH(n-propyl)$_2$ | —CH$_3$ |
| 4-dimethylamino-6-methyl-3-pyridyl | —CH(n-propyl)$_2$ | —CH$_3$ |
| 4-dimethylamino-3-pyridyl | —CH(n-propyl)$_2$ | —CH$_3$ |
| 2,4-dichlorophenyl | —CH(n-propyl)(CH$_2$OCH$_3$) | —CH$_3$ |
| 2-chloro-4-methyl-phenyl | —CH(n-propyl)(CH$_2$OCH$_3$) | —CH$_3$ |
| 2-methyl-4-chloro-phenyl | —CH(n-propyl)(CH$_2$OCH$_3$) | —CH$_3$ |
| 2,4,6-trimethyl-phenyl | —CH(n-propyl)(CH$_2$OCH$_3$) | —CH$_3$ |
| 2-chloro-4-methoxy-phenyl | —CH(n-propyl)(CH$_2$OCH$_3$) | —CH$_3$ |
| 2-methyl-4-methoxy-phenyl | —CH(n-propyl)(CH$_2$OCH$_3$) | —CH$_3$ |
| 2,4-dimethoxy-phenyl | —CH(n-propyl)(CH$_2$OCH$_3$) | —CH$_3$ |
| 4-dimethylamino-2-methyl-3-pyridyl | —CH(n-propyl)(CH$_2$OCH$_3$) | —CH$_3$ |
| 4-dimethylamino-6-methyl-3-pyridyl | —CH(n-propyl)(CH$_2$OCH$_3$) | —CH$_3$ |
| 4-dimethylamino-3-pyridyl | —CH(n-propyl)(CH$_2$OCH$_3$) | —CH$_3$ |
| 2,4-dichlorophenyl | —CH(benzyl)(CH$_2$OCH$_3$) | —CH$_3$ |
| 2-chloro-4-methyl-phenyl | —CH(benzyl)(CH$_2$OCH$_3$) | —CH$_3$ |
| 2-methyl-4-chloro-phenyl | —CH(benzyl)(CH$_2$OCH$_3$) | —CH$_3$ |
| 2,4,6-trimethyl-phenyl | —CH(benzyl)(CH$_2$OCH$_3$) | —CH$_3$ |
| 2-chloro-4-methoxy-phenyl | —CH(benzyl)(CH$_2$OCH$_3$) | —CH$_3$ |
| 2-methyl-4-methoxy-phenyl | —CH(benzyl)(CH$_2$OCH$_3$) | —CH$_3$ |
| 2,4-dimethoxy-phenyl | —CH(benzyl)(CH$_2$OCH$_3$) | —CH$_3$ |
| 4-dimethylamino-2-methyl-3-pyridyl | —CH(benzyl)(CH$_2$OCH$_3$) | —CH$_3$ |
| 4-dimethylamino-6-methyl-3-pyridyl | —CH(benzyl)(CH$_2$OCH$_3$) | —CH$_3$ |
| 4-dimethylamino-3-pyridyl | —CH(benzyl)(CH$_2$OCH$_3$) | —CH$_3$ |
| 2,4-dichlorophenyl | —CH(CH$_2$OR)$_2$ | —CH$_3$ |
| 2-chloro-4-methyl-phenyl | —CH(CH$_2$OR)$_2$ | —CH$_3$ |
| 2-methyl-4-chloro-phenyl | —CH(CH$_2$OR)$_2$ | —CH$_3$ |
| 2,4,6-trimethyl-phenyl | —CH(CH$_2$OR)$_2$ | —CH$_3$ |
| 2-chloro-4-methoxy-phenyl | —CH(CH$_2$OR)$_2$ | —CH$_3$ |
| 2-methyl-4-methoxy-phenyl | —CH(CH$_2$OR)$_2$ | —CH$_3$ |
| 2,4-dimethoxy-phenyl | —CH(CH$_2$OR)$_2$ | —CH$_3$ |
| 4-dimethylamino-2-methyl-3-pyridyl | —CH(CH$_2$OR)$_2$ | —CH$_3$ |
| 4-dimethylamino-6-methyl-3-pyridyl | —CH(CH$_2$OR)$_2$ | —CH$_3$ |
| 4-dimethylamino-3-pyridyl | —CH(CH$_2$OR)$_2$ | —CH$_3$ |
| 2,4-dichlorophenyl | —CH(CH$_2$OR)(ethyl) | —CH$_3$ |
| 2-chloro-4-methyl-phenyl | —CH(CH$_2$OR)(ethyl) | —CH$_3$ |
| 2-methyl-4-chloro-phenyl | —CH(CH$_2$OR)(ethyl) | —CH$_3$ |
| 2,4,6-trimethyl-phenyl | —CH(CH$_2$OR)(ethyl) | —CH$_3$ |

TABLE 1-continued

REPRESENTATIVE AR, $R_1$ AND $R_2$ GROUPS OF STRUCTURE (I)

| Ar | $R_1$ | $R_2$ |
|---|---|---|
| 2-chloro-4-methoxy-phenyl | —CH(CH$_2$OR)(ethyl) | —CH$_3$ |
| 2-methyl-4-methoxy-phenyl | —CH(CH$_2$OR)(ethyl) | —CH$_3$ |
| 2,4-dimethoxy-phenyl | —CH(CH$_2$OR)(ethyl) | —CH$_3$ |
| 4-dimethylamino-2-methyl-3-pyridyl | —CH(CH$_2$OR)(ethyl) | —CH$_3$ |
| 4-dimethylamino-6-methyl-3-pyridyl | —CH(CH$_2$OR)(ethyl) | —CH$_3$ |
| 4-dimethylamino-3-pyridyl | —CH(CH$_2$OR)(ethyl) | —CH$_3$ |
| 2,4-dichlorophenyl | —CH(CH$_2$OR)(n-butyl) | —CH$_3$ |
| 2-chloro-4-methyl-phenyl | —CH(CH$_2$OR)(n-butyl) | —CH$_3$ |
| 2-methyl-4-chloro-phenyl | —CH(CH$_2$OR)(n-butyl) | —CH$_3$ |
| 2,4,6-trimethyl-phenyl | —CH(CH$_2$OR)(n-butyl) | —CH$_3$ |
| 2-chloro-4-methoxy-phenyl | —CH(CH$_2$OR)(n-butyl) | —CH$_3$ |
| 2-methyl-4-methoxy-phenyl | —CH(CH$_2$OR)(n-butyl) | —CH$_3$ |
| 2,4-dimethoxy-phenyl | —CH(CH$_2$OR)(n-butyl) | —CH$_3$ |
| 4-dimethylamino-2-methyl-3-pyridyl | —CH(CH$_2$OR)(n-butyl) | —CH$_3$ |
| 4-dimethylamino-6-methyl-3-pyridyl | —CH(CH$_2$OR)(n-butyl) | —CH$_3$ |
| 4-dimethylamino-3-pyridyl | —CH(CH$_2$OR)(n-butyl) | —CH$_3$ |
| 2,4-dichlorophenyl | —CH(CH$_2$OR)(tert-butyl) | —CH$_3$ |
| 2-chloro-4-methyl-phenyl | —CH(CH$_2$OR)(tert-butyl) | —CH$_3$ |
| 2-methyl-4-chloro-phenyl | —CH(CH$_2$OR)(tert-butyl) | —CH$_3$ |
| 2,4,6-trimethyl-phenyl | —CH(CH$_2$OR)(tert-butyl) | —CH$_3$ |
| 2-chloro-4-methoxy-phenyl | —CH(CH$_2$OR)(tert-butyl) | —CH$_3$ |
| 2-methyl-4-methoxy-phenyl | —CH(CH$_2$OR)(tert-butyl) | —CH$_3$ |
| 2,4-dimethoxy-phenyl | —CH(CH$_2$OR)(tert-butyl) | —CH$_3$ |
| 4-dimethylamino-2-methyl-3-pyridyl | —CH(CH$_2$OR)(tert-butyl) | —CH$_3$ |
| 4-dimethylamino-6-methyl-3-pyridyl | —CH(CH$_2$OR)(tert-butyl) | —CH$_3$ |
| 4-dimethylamino-3-pyridyl | —CH(CH$_2$OR)(tert-butyl) | —CH$_3$ |
| 2,4-dichlorophenyl | —CH(CH$_2$OR)(4-chloro-benzyl) | —CH$_3$ |
| 2-chloro-4-methyl-phenyl | —CH(CH$_2$OR)(4-chloro-benzyl) | —CH$_3$ |
| 2-methyl-4-chloro-phenyl | —CH(CH$_2$OR)(4-chloro-benzyl) | —CH$_3$ |
| 2,4,6-trimethyl-phenyl | —CH(CH$_2$OR)(4-chloro-benzyl) | —CH$_3$ |
| 2-chloro-4-methoxy-phenyl | —CH(CH$_2$OR)(4-chloro-benzyl) | —CH$_3$ |
| 2-methyl-4-methoxy-phenyl | —CH(CH$_2$OR)(4-chloro-benzyl) | —CH$_3$ |
| 2,4-dimethoxy-phenyl | —CH(CH$_2$OR)(4-chloro-benzyl) | —CH$_3$ |
| 4-dimethylamino-2-methyl-3-pyridyl | —CH(CH$_2$OR)(4-chloro-benzyl) | —CH$_3$ |
| 4-dimethylamino-6-methyl-3-pyridyl | —CH(CH$_2$OR)(4-chloro-benzyl) | —CH$_3$ |
| 4-dimethylamino-3-pyridyl | —CH(CH$_2$OR)(4-chloro-benzyl) | —CH$_3$ |
| 2,4-dichlorophenyl | —CH(CH$_2$OR)(CH$_2$CH$_2$SCH$_3$) | —CH$_3$ |
| 2-chloro-4-methyl-phenyl | —CH(CH$_2$OR)(CH$_2$CH$_2$SCH$_3$) | —CH$_3$ |
| 2-methyl-4-chloro-phenyl | —CH(CH$_2$OR)(CH$_2$CH$_2$SCH$_3$) | —CH$_3$ |
| 2,4,6-trimethyl-phenyl | —CH(CH$_2$OR)(CH$_2$CH$_2$SCH$_3$) | —CH$_3$ |
| 2-chloro-4-methoxy-phenyl | —CH(CH$_2$OR)(CH$_2$CH$_2$SCH$_3$) | —CH$_3$ |
| 2-methyl-4-methoxy-phenyl | —CH(CH$_2$OR)(CH$_2$CH$_2$SCH$_3$) | —CH$_3$ |
| 2,4-dimethoxy-phenyl | —CH(CH$_2$OR)(CH$_2$CH$_2$SCH$_3$) | —CH$_3$ |
| 4-dimethylamino-2-methyl-3-pyridyl | —CH(CH$_2$OR)(CH$_2$CH$_2$SCH$_3$) | —CH$_3$ |
| 4-dimethylamino-6-methyl-3-pyridyl | —CH(CH$_2$OR)(CH$_2$CH$_2$SCH$_3$) | —CH$_3$ |
| 4-dimethylamino-3-pyridyl | —CH(CH$_2$OR)(CH$_2$CH$_2$SCH$_3$) | —CH$_3$ |
| 2,4-dichlorophenyl | —CH(CH$_2$CH$_3$)(CH$_2$Obenzyl) | —CH$_3$ |
| 2-chloro-4-methyl-phenyl | —CH(CH$_2$CH$_3$)(CH$_2$Obenzyl) | —CH$_3$ |
| 2-methyl-4-chloro-phenyl | —CH(CH$_2$CH$_3$)(CH$_2$Obenzyl) | —CH$_3$ |
| 2,4,6-trimethyl-phenyl | —CH(CH$_2$CH$_3$)(CH$_2$Obenzyl) | —CH$_3$ |
| 2-chloro-4-methoxy-phenyl | —CH(CH$_2$CH$_3$)(CH$_2$Obenzyl) | —CH$_3$ |
| 2-methyl-4-methoxy-phenyl | —CH(CH$_2$CH$_3$)(CH$_2$Obenzyl) | —CH$_3$ |
| 2,4-dimethoxy-phenyl | —CH(CH$_2$CH$_3$)(CH$_2$Obenzyl) | —CH$_3$ |
| 4-dimethylamino-2-methyl-3-pyridyl | —CH(CH$_2$CH$_3$)(CH$_2$Obenzyl) | —CH$_3$ |
| 4-dimethylamino-6-methyl-3-pyridyl | —CH(CH$_2$CH$_3$)(CH$_2$Obenzyl) | —CH$_3$ |
| 4-dimethylamino-3-pyridyl | —CH(CH$_2$CH$_3$)(CH$_2$Obenzyl) | —CH$_3$ |
| 2,4-dichlorophenyl | —CH(n-butyl)$_2$ | —CH$_3$ |
| 4-isopropyl-phenyl | —CH(n-propyl)$_2$ | —CH$_3$ |
| 4-chloro-phenyl | —CH(n-propyl)$_2$ | —CH$_3$ |
| 4-methoxy-phenyl | —CH(n-propyl)$_2$ | —CH$_3$ |
| 4-t-butyl-phenyl | —CH(n-propyl)$_2$ | —CH$_3$ |
| 2-benzofuranyl | —CH(n-propyl)$_2$ | —CH$_3$ |
| 3,4-dimethoxy-phenyl | —CH(n-propyl)$_2$ | —CH$_3$ |

TABLE 1-continued

REPRESENTATIVE AR, $R_1$ AND $R_2$ GROUPS OF STRUCTURE (I)

| Ar | $R_1$ | $R_2$ |
|---|---|---|
| 2-chloro-phenyl | —CH(n-propyl)$_2$ | —CH$_3$ |
| 2-benzothiophenyl | —CH(n-propyl)$_2$ | —CH$_3$ |
| 4-trifluoromethyl-phenyl | —CH(n-propyl)$_2$ | —CH$_3$ |
| 4-methylthio-phenyl | —CH(n-propyl)$_2$ | —CH$_3$ |
| 3-isopropyl-6-methoxy-phenyl | —CH(n-propyl)$_2$ | —CH$_3$ |
| 4-trifluoromethoxy-phenyl | —CH(n-propyl)$_2$ | —CH$_3$ |
| 3-trifluoromethyl-phenyl | —CH(n-propyl)$_2$ | —CH$_3$ |
| dibenzofuranyl | —CH(n-propyl)$_2$ | —CH$_3$ |
| 2,4-dichlorophenyl | 3-methylcyclohexyl | —CH$_3$ |

NOTE:
Each occurrence of R in this Table is independently selected from a $C_{1-6}$ alkyl, such as methyl or ethyl.

The compounds of the present invention may be prepared by known organic synthesis techniques, including the methods described in more detail in the Examples, and may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., [$^{125}$I] tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the IC$_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 μM. In a preferred embodiment of this invention, a CRF receptor antagonist has a $K_i$ of less than 1 μM, and more preferably less than 0.25 μM (i.e., 250 nM).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various disease states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment, compounds of this invention and their analogs may be used as Positron Emission Tomography (PET) ligands, Single Photon Emission Computed Tomography (SPECT) ligands, or other diagnostic radiopharmaceutical agents. Incorporation of an appropriate isotope (such as $^{11}$C or $^{18}$F for PET or $^{125}$I in the case of SPECT) may provide an agent useful for the diagnosis or therapeutic management of a patient. In addition, use of a compound of the present invention may provide a physiological, functional, or biological assessment of a patient or provide disease or pathology detection and assessment.

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder— that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

The following examples are provided for purposes of illustration, not limitation.

EXAMPLES

The CRF receptor antagonists of this invention may be prepared by the methods disclosed in Examples 1–2. Example 3 presents a method for determining the receptor binding activity ($K_i$) of compounds of this invention, while Example 4 discloses an assay for screening compounds of this invention for CRF-stimulated adenylate cyclase activity.

Example 1

Synthesis of Representative Compounds of Structure (IA)

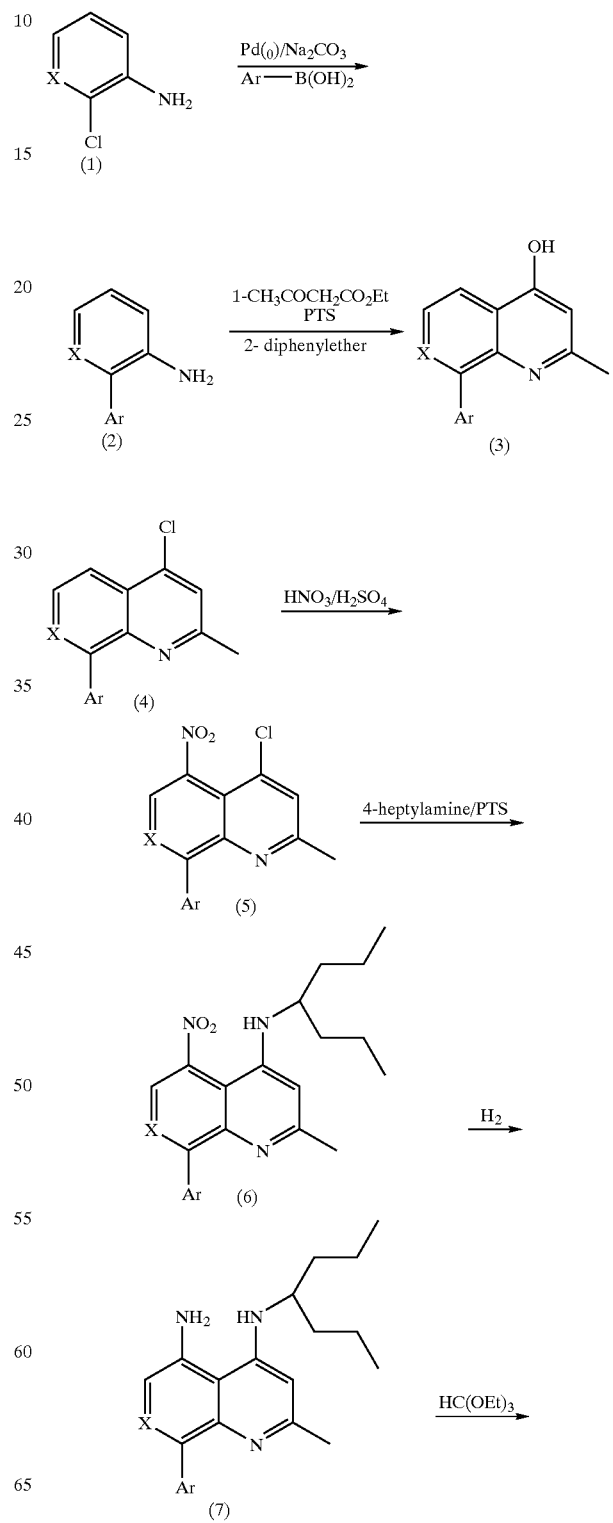

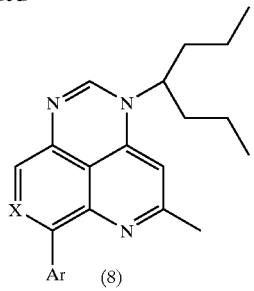

3-amino-2-(2,4,6-trimethyl)phenyl pyridine (2) (when X = N and Ar = 2,4,6-trimethylphenyl)

A mixture of 3-amino-2-chloropyridine (1) (2 g, 15 mmol, 1 eq.), trimethylphenylboronic acid ("Ar—B(OH)$_2$") (2.3 g, 14 mmol, 0.9 eq.), cesium fluoride (4.7 g, 31 mmol, 2 eq.) and tetrakis(triphenylphosphine)palladium(0) (0.5 g, 4% mol) were heated at reflux in anhydrous DME under N$_2$ atmosphere overnight. After cooling down at room temperature, solvents were evaporated under reduced pressure. The residue was dissolved in ethyl acetate, washed with water (3×50 mL). The aqueous phases were combined, extracted with ethyl acetate (3×50 mL). The organic phases were combined, extracted with a brine solution (50 mL) and dried with Na$_2$SO$_4$. Compound (2) was purified by liquid chromatography on silica gel with hexanes/ethyl acetate 8/2 as eluent mixture (Rf=0.4). 3 g of a transparent oil was obtained. LC/MS (positive) 213 (M+1).
3-amino-2-(2,4-dichloro)phenyl pyridine (2') (when X=M and Ar=2,4-dichlorophenyl)

The same procedure was employed as for compound (2) above, but using 2,4-dichlorophenylboronic acid in place of Ar—B(OH)$_2$. LC/MS (positive) 238 (M+1).
4-hydroxy 2-methyl 8-(2,4,6-trimethyl)phenly-1,7-naphthyridine (3)

A solution of 1.5 g of 3-amino-2-(2,4,6-trimethyl)phenyl pyridine (2) (7.07 mmol, 1 eq.), 1.6 mL of ethylacetoacetate (12 mmol, 1.7 eq.) and a 200 mg of paratoluenesulfonic acid in 40 mL of m-xylene was refluxed with a Dean-Stark trap for about 1.5 hour. The m-xylene was removed. The residue was added to 4 mL of diphenylether and heated until all the intermediate compound reacted (about 10 min). The ring-closure was followed by LC/MS. After cooling down at room temperature, 100 mL of hexanes were added allowing compound (3) to crash out and used without further purification. LC/MS (positive) 279 (M+1).
4-hydroxy-2-methyl 8-(2,4-dichloro)phenyl-1,7-naphthyridine (3')

Same procedure was employed as for compound (3) above, but using compound (2') in place of compound (2). LC/MS positive 305 (M+1).
4-chloro 2-methyl 8-(2,4,6-trimethyl)phenyl-1,7-naphthyridine (4)

4-hydroxy-2-methyl-8-trimethylphenyl-1,7-naphthyridine (3) was refluxed in 10 mL of POCl$_3$ for 5 hours. After cooling down at room temperature, the reaction mixture was poured on ice and neutralized with a 6N NaOH solution. The product was extracted with ethyl acetate (3×50 mL). The organic phases were combined, washed with water (2×50 mL), a brine solution (1×50 mL) and dried with sodium thiosulfate. Compound (4) was purified by liquid chromatography on silica gel (hexanes/ethyl acetate 9/1, Rf 0.6). The reaction was quantitative. LC/MS (positive) 297 (M+1).

4-chloro-2-methyl-8-(2,4-dichloro)phenyl-1,7-naphthyridine (4')

Same procedure was employed as for compound (4) above, but using compound (3') in place of compound (3). LC/MS (positive) 342 (M+1).
4-chloro-2-methyl-5-nitro-8-(2,4,6-trimethyl)phenyl-1,7-naphthyridine (5)

4-chloro-2-methyl-8-trimethylphenyl-1,7-naphthyridine (4) (521 mg, 1.76 mmol, 1 eq.) was added to 0.9 mL of sulfuric acid 97% in an ice-bath. The mixture was heated at 55° C. and 124 μl of nitric acid 70% (1.93 mmol, 1.1 eq.) were added. The reaction mixture was then stirred at 55 C. for 5 hours, cooled down, poured into 20 mL of ice water and partially neutralized with 6N NaOH solution. The product was then extracted with ethyl acetate (3×50 mL). The organic phases were combined, washed with water (2×50 mL), a brine solution (1×50 mL) and dried with sodium thiosulfate. Compound (5) was used with further purification for the following step. LC/MS (positive) 342 (M+1).
4-chloro-2-methyl-5-nitro-8-(2,4-dichloro)phenyl-1,7-naphthyridine (5')

Same procedure was employed as for compound (5) above but using compound (4') in place of compound (4).
4-(N-4-heptyl amino)-2-methyl-5-nitro-8-(2,4,6-trimethyl)phenyl-1,7-naphthyridine (6)

4-chloro-2-methyl-5-nitro-8-(2,4,6-trimethyl)phenyl-1,7-naphthyridine (5) was heated in an excess of 4-heptylamine (0.5 mL) with paratoluene sulfonic acid at 165° C. in a reacti-vac overnight. After cooling down at room temperature, the reaction mixture was diluted in ethyl acetate and passed through a plug of silica gel. Solvents were evaporated and compound (6) used in the following step without purification. The reaction was quantitative. LCV/MS (positive) 421 (M+1).
4-(N-4-heptyl amino)-2-methyl-5-nitro-8-(2,4-dichloro)phenyl-1,7-naphthyridine (6')

Same procedure was employed as for compound (6) above, but using compound (5') in place of compound (5).
4-(N-4-heptylamino)-2-methyl-5-amino-8-(2,4,6-trimethyl)phenyl-1,7-naphthyridine (7)

4-(N-4-heptylamino)-2-methyl-5-nitro-8-(2,4,6-trimethyl)phenyl-1,7-naphthyridine (6) was added to a suspension of palladium on carbon (10% and a drop of acetic acid in methanol. The mixture was shaken for 20 hours under hydrogen pressure (35 psi) at room temperature. The catalyst was removed by filtration under celite and the solvents evaporated. Compound (7) was used in the following step without purification. The reaction was quantitative. LC/MS (positive) 391 (M+1).
4-(N-4-heptylamino)-2-methyl-5-amino-8-(2,4-dichloro)phenyl-1,7-naphthyridine (7')

To a solution of 4-(N-4-heptylamino)-2-methyl-5-nitro-8-(2,4-dichloro)phenyl-1,7-naphthyridine (6') (153 mg, 0.36 mmol, 1 eq.) in THF (8.5 mL) was added a solution of Na$_2$—S$_2$—O$_3$ in water (4.3 mL). The reaction mixture was heated at 60° C. for 2 hours. After cooling down at room temperature th4 product was extracted with ethyl acetate (3×50 mL). The organic phases were combined, washed with water (2×50 mL), a brine solution (1×50 mL) and dried with sodium thiosulfate. Solvents were evaporated and compound (7') was purified by PTLC (ethyl acetate/hexanes 1/9 Rf 0.1).
Compound (8)

100 mg of 4-(N-4-heptylamino)-2-methyl-5-amino-8-(2,4,6-trimethyl)phenyl-1,7-naphthyridine (7) (0.4 mmol) was treated with triethylorthoformate (2 mL) at reflux for 16 hours. After cooling down at room temperature and evaporation of the solvent, the product was extracted with ethyl acetate (3×20 mL). The organic phases were combined, washed with water (10 mL), a brine solution (10 mL) and dried with sodium thiosulfate. Solvents were evaporated and compound (8) was purified by PTLC (ethyl acetate/hexanes 1/1). LC/MS (positive) 400 (M+1).

Compound (8')

Same procedure was employed as for compound (8), but using compound (7') in place of compound (7).

Structure (Ia")

Compounds of structure (Ia") may be made by the same procedures as disclosed above, but employing 2-chloro-aniline as compound (1) in place of 3-amino-2-chloropyridine. By this technique, the compounds listed in the following Table 2 were prepared.

TABLE 2

REPRESENTATIVE COMPOUNDS OF STRUCTURE (I$_A$")

| Ar | R$_1$ | R$_2$ | MW |
|---|---|---|---|
| 2,4-dichlorophenyl | —CH(n-propyl)$_2$ | —CH$_3$ | 426 |
| 4,6-dimethoxy-phenyl | —CH(n-propyl)$_2$ | —CH$_3$ | 417 |
| 4-methoxy-6-methyl-phenyl | —CH(n-propyl)$_2$ | —CH$_3$ | 401 |
| 2,4-dichlorophenyl | —CH(ethyl)$_2$ | —CH$_3$ | 398 |
| 2,4-dichlorophenyl | —CH(n-butyl)$_2$ | —CH$_3$ | 454 |
| 4-isopropyl-phenyl | —CH(n-propyl)$_2$ | —CH$_3$ | 400 (M + 1) |
| 4-chloro-phenyl | —CH(n-propyl)$_2$ | —CH$_3$ | 393 (M + 1) |
| 4-methoxy-phenyl | —CH(n-propyl)$_2$ | —CH$_3$ | 388 (M + 1) |
| 4-t-butyl-phenyl | —CH(n-propyl)$_2$ | —CH$_3$ | 414 (M + 1) |
| 2-benzofuranyl | —CH(n-propyl)$_2$ | —CH$_3$ | 398 (M + 1) |
| 3,4-dimethoxy-phenyl | —CH(n-propyl)$_2$ | —CH$_3$ | 392 |
| 2-chloro-phenyl | —CH(n-propyl)$_2$ | —CH$_3$ | 399 |
| 2-benzothiophenyl | —CH(n-propyl)$_2$ | —CH$_3$ | 413 |
| 4-trifluoromethyl-phenyl | —CH(n-propyl)$_2$ | —CH$_3$ | 425 |
| 4-methylthio-phenyl | —CH(n-propyl)$_2$ | —CH$_3$ | 403 |
| 5-isopropyl-2-methoxy-phenyl | —CH(n-propyl)$_2$ | —CH$_3$ | 429 |
| 4-trifluoromethoxy-phenyl | —CH(n-propyl)$_2$ | —CH$_3$ | 441 |
| 3-trifluoromethyl-phenyl | —CH(n-propyl)$_2$ | —CH$_3$ | 425 |
| dibenzofuranyl | —CH(n-propyl)$_2$ | —CH$_3$ | 447 |
| 2,4-dichlorophenyl | 3-methylcyclohexyl | —CH$_3$ | 424 |

Example 2

Synthesis of Representative Compounds of Structure (IB) and (IC)

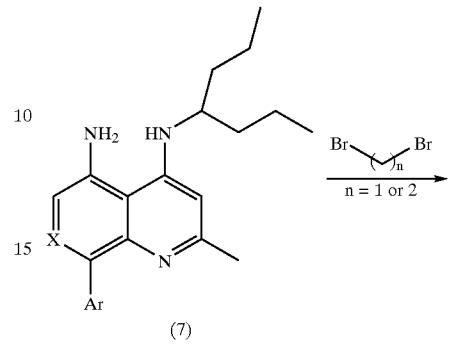

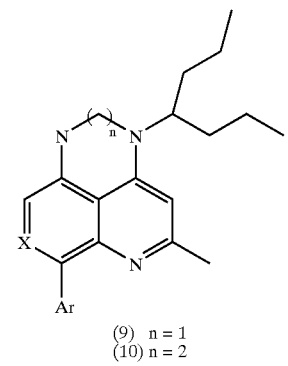

Structures (Ib') and (Ic')

Compound (9)

100 mg of 4-(N-4-heptylamino)-2-methyl-5-amino-8-(2,4,6-trimethyl)phenyl-1,7-naphthyridine (7) (0.4 mmol), 30 µl of dibromopropane and 100 mg of K$_2$CO4 were dissolved in 2 mL of 2-butanone. The reaction mixture was heated at 85° C. for 4 hours in a reacti-vac. After cooling down at room temperature compound (9) was extracted with ethyl acetate (3×20 mL). The organic phases were combined, washed with water (10 mL), a brine solution (10 mL) and dried with sodium thiosulfate. Solvents were evaporated and compound (9) was purified by PTLC (ethyl acetate/hexanes 1/1).

Compound (9')

Same procedure was employed as for compound (9), but using compound (7') in place of compound (7).

Compound (10)

100 mg of 4-(4-heptylamino)-2-methyl-5-amino-8-(2,4,6-trimethyl)phenyl-1,7-naphthyridine (7) (0.4 mmol), 30 µl of dibromopropane and 100 mg of K$_2$CO$_3$ were dissolved in 2 mL of 2-butanone. The reaction mixture was heated at 85° C. for 4 hours in a reacti-vac. After cooling down at room temperature compound (10) was extracted with ethyl acetate (3×20 mL). The organic phases were combined, washed with water (10 mL), a brine solution (10 mL) and dried with sodium thiosulfate. Solvents were evaporated and compound (10) was purified by PTLC (ethyl acetate/hexanes 1/1). LC/MS (positive) 414 (M+1).

Compound (10')

Same procedure was employed as for compound (10), but using compound (7') in place of compound (7).

Structures (Ib") and (Ic")

Compounds of structure (Ib") and (Ic") may be made by the same procedures as disclosed above, but employing, 2-chloro-aniline as compound (1) (X=CH) in place of 3-amino-2-chloropyridine. By this technique the following representative compound of structure (Ic") was made: Ar=2, 4-dichlorophenyl, $R_1$=—CH(n-propyl)$_2$ and $R_2$=—CH$_3$ (MW=442).

Example 3

Representative Compounds Having CRF Receptor Binding Activity

The compounds of this invention may be evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 mL Eppendorf tubes using approximately 1×10$^6$ cells per tube stably transfected with human CRF receptors. Each tube receives about 0.1 mL of assay buffer (e.g., Dulbecco's phosphate buffered saline, 10 mM magnesium chloride, 20 µM bacitracin) with or without unlabeled sauvagine, urotensin I or CRF (final concentration, 1 µM) to determine nonspecific binding, 0.1 mL of [$^{125}$I] tyrosine-ovine CRF (final concentration ~200 pM or approximately the $K_D$ as determined by Scatchard analysis) and 0.1 mL of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the non-linear least-square curve-fitting program LIGAND of Munson and Rodbard (*Anal. Biochem.* 107:220, 1990).

Example 4

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 mL: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 µl of a solution of 95% ethanol and 20 mM aqueous hydrochloric acid is added to each well and the resulting suspensions are incubated at −20° C. for 16 to 18 hours. The solution is removed into 1.5 mL Eppendorf tubes and the wells washed with an additional 200 µl of ethanol/aqueous hydrochloric acid and pooled with the first fraction. The samples are lyophilized and then resuspended with 500 µl sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds (10$^{-12}$ to 10$^{-6}$ M).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound having the following structure:

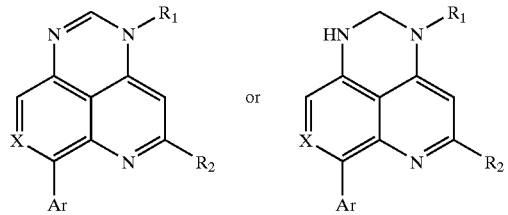

including stereoisomers and pharmaceutically acceptable salts thereof, wherein:

$R_1$ is —CH($R_4$)($R_5$);

$R_2$ is $C_{1-6}$alkyl;

$R_3$ is hydrogen or $C_{1-6}$alkyl;

$R_4$ is hydrogen, $C_{1-6}$alkyl, mono- or di($C_{3-6}$cycloalkyl) methyl, $C_{3-6}$cycloalkyl, $C_{3-6}$alkenyl, hydroxy$C_{1-6}$alkyl, $C_{1-6}$alkylcarbonyloxy$C_{1-6}$alkyl, or $C_{1-6}$alkyloxy$C_{1-6}$alkyl, and $R_5$ is $C_{1-8}$alkyl, mono- or di($C_{3-6}$cycloalkyl)methyl, Ar$^1$CH$_2$, $C_{3-6}$alkenyl, $C_{1-6}$alkyloxy$C_{1-6}$alkyl, hydroxy$C_{1-6}$alkyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl, —CH$_2$Obenzyl, or a radical of the formula —($C_{1-6}$alkanediyl))—O—CO—Ar$^1$, or $R_4$ and $R_5$ taken together with the carbon atom to which they are bonded form a $C_{5-8}$cycloalkyl optionally substituted with one or more substituents independently selected from $C_{1-6}$alkyl;

Ar is phenyl substituted with 1, 2 or 3 substituents independently selected from halo, $C_{1-6}$alkyl, trifluoromethyl, cyano, $C_{1-6}$alkyloxy, benzyloxy, $C_{1-6}$alkylthio, nitro, amino, and mono- or di($C_{1-6}$alkyl)amino; or an aromatic $C_{3-12}$heterocycle optionally substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino, mono- or di($C_{1-6}$alkyl)amino, and piperidinyl; and Ar$^1$is phenyl, pyridinyl, or phenyl substituted with 1, 2 or 3 substituents independently selected from halo, $C_{1-6}$alkyl, $C_{1-6}$alkyloxy, di($C_{1-6}$alkyl)amino$C_{1-6}$alkyl, trifluoromethyl and $C_{1-6}$alkyl substituted with morpholinyl.

2. The compound of claim 1 having the structure:

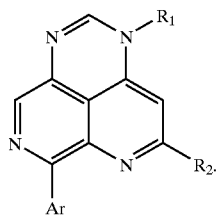

3. The compound of claim 1 having the structure:

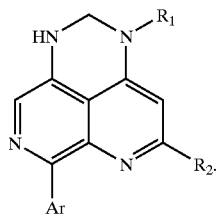

4. The compound of claim 1 wherein Ar is 2,4-dichlorophenyl.

5. The compound of claim 1 wherein Ar is 2-chloro-4-methyl-phenyl.

6. The compound of claim 1 wherein Ar is 2-methyl-4-chloro-phenyl.

7. The compound of claim 1 wherein Ar is 2,4,6-trimethyl-phenyl.

8. The compound of claim 1 wherein Ar is 2-chloro-4-methoxy-phenyl.

9. The compound of claim 1 wherein Ar is 2-methyl-4-methoxy-phenyl.

10. The compound of claim 1 wherein Ar is 2,4-dimethoxy-phenyl.

11. The compound of claim 1 wherein Ar is 4-dimethylamino-2-methyl-3-pyridyl.

12. The compound of claim 1 wherein Ar is 4-dimethylamino-6-methyl-3-pyridyl.

13. The compound of claim 1 wherein Ar is 4-dimethylamino-3-pyridyl.

14. The compound of claim 1 wherein $R_1$ is —CH(n-propyl)$_2$.

15. The compound of claim 1 wherein $R_1$ is —CH(n-propyl)(CH$_2$OCH$_3$).

16. The compound of claim 1 wherein $R_1$ is —CH(benzyl)(CH$_2$OCH$_3$).

17. The compound of claim 1 wherein $R_1$ is —CH(CH$_2$OR)$_2$ and each occurrence of R is independently selected from $C_{1-6}$alkyl.

18. The compound of claim 1 wherein $R_1$ is —CH(CH$_2$OR)(ethyl) and each occurrence of R is independently selected from $C_{1-6}$alkyl.

19. The compound of claim 1 wherein $R_1$ is —CH(CH$_2$OR)(n-butyl) and each occurrence of R is independently selected from $C_{1-6}$alkyl.

20. The compound of claim 1 wherein $R_1$ is —CH(CH$_2$OR)(tert-butyl) and each occurrence of R is independently selected from $C_{1-6}$alkyl.

21. The compound of claim 1 wherein $R_1$ is —CH(CH$_2$OR)(4-chloro-benzyl) and each occurrence of R is independently selected from $C_{1-6}$alkyl.

22. The compound of claim 1 wherein $R_1$ is —CH(CH$_2$OR)(CH$_2$CH$_2$SCH$_3$) and each occurrence of R is independently selected from $C_{1-6}$alkyl.

23. The compound of claim 1 wherein $R_1$ is —CH(CH$_2$CH$_3$)(CH$_2$Obenzyl).

24. The compound of claim 1 wherein $R_2$ is methyl.

25. The compound of claim 1 wherein $R_2$ is ethyl.

26. A composition comprising a compound of claim 1 in combination with a pharmaceutically acceptable carrier or diluent.

27. A method for treating stroke, anxiety, depression or irritable bowel syndrome in a warm-blooded animal, comprising administering to the animal an effective amount of the composition of claim 26.

28. The method of claim 27 wherein the disorder is stroke.

29. The method of claim 27 wherein the disorder is anxiety.

30. The method of claim 27 wherein the disorder is depression.

31. The method of claim 27 wherein the disorder is irritable bowel syndrome.

* * * * *